(12) United States Patent
Martone et al.

(10) Patent No.: US 11,504,147 B2
(45) Date of Patent: Nov. 22, 2022

(54) ARTICULATING MICROSURGICAL INSTRUMENT

(71) Applicant: Vascular Technology, Incorporated, Nashua, NH (US)

(72) Inventors: Stephen Martone, Nashua, NH (US); Trevor Jacob Laughlin, Minneapolis, MN (US); Rachana S. Suchdev, Hollis, NH (US); David Regan, Pelham, NH (US)

(73) Assignee: Vascular Technology, Incorporated, Nashua, NH (US)

( * ) Notice: Subject to any disclaimer, the term of this patent is extended or adjusted under 35 U.S.C. 154(b) by 861 days.

(21) Appl. No.: 16/413,181

(22) Filed: May 15, 2019

(65) Prior Publication Data

US 2019/0350607 A1   Nov. 21, 2019

Related U.S. Application Data

(60) Provisional application No. 62/673,468, filed on May 18, 2018.

(51) Int. Cl.
  *A61B 17/00*  (2006.01)
  *A61B 17/30*  (2006.01)
  (Continued)

(52) U.S. Cl.
  CPC .............. *A61B 17/30* (2013.01); *A61B 8/488* (2013.01); *A61B 17/295* (2013.01);
  (Continued)

(58) Field of Classification Search
  CPC ..... A61B 8/0816; A61B 8/448; A61B 8/4483; A61B 17/30
  See application file for complete search history.

(56) References Cited

U.S. PATENT DOCUMENTS

| | | | | |
|---|---|---|---|---|
| 5,318,525 A | * | 6/1994 | West | A61B 18/1492 604/95.04 |
| 5,398,689 A | * | 3/1995 | Connor | G01N 29/265 600/459 |

(Continued)

FOREIGN PATENT DOCUMENTS

| | | |
|---|---|---|
| CA | 2984729 | 2/2017 |
| CA | 2978285 | 4/2018 |

(Continued)

OTHER PUBLICATIONS

International Preliminary Report on Patentability received for PCT/US2019/032455. dated Dec. 3, 2020. 9 pages.

(Continued)

*Primary Examiner* — Eyamindae C Jallow
(74) *Attorney, Agent, or Firm* — Finch & Maloney PLLC

(57) ABSTRACT

An apparatus and method for an articulating microsurgical instrument is disclosed herein. The articulating microsurgical instrument may be configured to be operable with a Doppler probe, bone grasper, soft tissue grasper/dissector, scissors, flexible forceps, or a suction/irrigation line configured to provide tools within a surgical location that can be adjusted to a desired angle of operation. A tip assembly may comprise an articulating portion at a distal tip and the articulating portion may be configured to deflect upon actuation of an articulation control. The articulation control may be a trigger assembly or a roller wheel. A bayonet-style handle may include a set of posts configured to interact with the one or more control wires during actuation of the articulation control. One or more control wires may be housed in a lumen and actuated using a articulation control of a handle assembly.

16 Claims, 15 Drawing Sheets

(51) Int. Cl.
*A61B 8/08* (2006.01)
*A61B 17/295* (2006.01)
*A61B 17/3201* (2006.01)
*A61B 17/88* (2006.01)
*A61B 17/29* (2006.01)
*A61B 34/00* (2016.01)

(52) U.S. Cl.
CPC .......... *A61B 17/3201* (2013.01); *A61B 17/88* (2013.01); *A61B 17/2909* (2013.01); *A61B 34/71* (2016.02); *A61B 2017/0023* (2013.01); *A61B 2017/00314* (2013.01); *A61B 2017/00323* (2013.01); *A61B 2017/00327* (2013.01); *A61B 2017/00345* (2013.01); *A61B 2017/00367* (2013.01); *A61B 2017/00389* (2013.01); *A61B 2017/00738* (2013.01); *A61B 2017/305* (2013.01); *A61B 2217/005* (2013.01); *A61B 2217/007* (2013.01)

(56) References Cited

U.S. PATENT DOCUMENTS

| | | | |
|---|---|---|---|
| 5,782,828 A * | 7/1998 | Chen | A61B 18/1492 606/41 |
| 5,888,198 A * | 3/1999 | Eggers | A61B 18/1482 604/114 |
| 6,036,645 A * | 3/2000 | Drost | A61B 8/12 600/459 |
| 6,641,539 B2 * | 11/2003 | Hirooka | A61B 8/4483 600/459 |
| 7,662,128 B2 | 2/2010 | Salcudean et al. | |
| 9,901,344 B2 | 2/2018 | Moore et al. | |
| 10,004,505 B2 | 6/2018 | Moore et al. | |
| 10,004,498 B2 | 8/2018 | Bockrath et al. | |
| 2003/0045768 A1 | 3/2003 | Hirooka et al. | |
| 2008/0091228 A1 | 4/2008 | Douglas et al. | |
| 2010/0312186 A1 | 12/2010 | Suchdev et al. | |
| 2016/0113729 A1 | 4/2016 | Burg et al. | |
| 2017/0266357 A1 | 9/2017 | Douglas et al. | |
| 2017/0319211 A1 | 11/2017 | Moore et al. | |
| 2017/0319273 A1 | 11/2017 | Wu et al. | |
| 2017/0340396 A1 | 11/2017 | Romo et al. | |
| 2018/0001057 A1 | 1/2018 | Mcweeney | |
| 2018/0056040 A1 | 3/2018 | Fenech et al. | |

FOREIGN PATENT DOCUMENTS

| | | |
|---|---|---|
| EP | 0876796 | 11/1998 |
| EP | 1836986 A2 | 9/2007 |
| EP | 2408509 | 1/2012 |
| EP | 2609886 A2 | 7/2013 |
| EP | 3060289 | 8/2016 |
| EP | 3120750 | 1/2017 |
| EP | 3205298 | 8/2017 |
| JP | 2001224595 A | 8/2001 |
| JP | 2013138864 A | 7/2013 |
| WO | 2007089676 A1 | 8/2007 |
| WO | 2010107916 | 9/2010 |
| WO | 2015061674 | 4/2015 |

OTHER PUBLICATIONS

PCT Search Report and Written Opinion for PCT Application No. PCT/US2019/032455 filed on May 15, 2019, 16 pages, dated Jul. 31, 2019.
Notice for Reasons For Rejection received for JP Application No. 2020-565905, dated Oct. 19, 2021. 10 pages including English translation.
Notice of Examination received for CN Application No. 3,098,625, dated Dec. 2, 2021. 4 pages.
Examination Report No. 2 received for AU patent application No. 2019271204, dated Sep. 20, 2021. 4 pages.

* cited by examiner

ARTICULATING MICROSURGICAL INSTRUMENT

CROSS-REFERENCE TO RELATED APPLICATIONS

This application claims priority under 35 USC § 119(e) to U.S. Provisional Patent Application No. 62/673,468 entitled "Articulating Microsurgical Instrument," filed on May 18, 2018, which is incorporated by reference herein in its entirety.

TECHNICAL FIELD

The present disclosure relates generally to medical devices. More particularly, some embodiments of the present disclosure relate to manipulatable sheaths configured with Doppler detection.

BACKGROUND

Articulating microsurgical instruments may be implemented in various types of surgeries, including neurosurgery, ear nose and throat (ENT) procedures, and cardiovascular procedures, for example. A surgeon, by holding the hand piece in their hand, can manipulate the working end to perform a desired task. Some conventional medical instruments utilize a flexible needle along with an ultrasound device external to the patient to measure spatial location of echos that contain a Doppler shift.

SUMMARY

The present disclosure provides a microsurgical instrument comprising one or more of the following features: (1) a manipulatable elongate member configured with Doppler detection; (2) one or more control wires configured to interact with an articulation control; (3) a bayonet-style handle; (4) an articulating portion at a distal tip; and (5) a set of posts internal to a housing assembly configured to interact with the one or more control wires during actuation of an articulation control. Bayonet-style handle, as used herein, is defined as a handle with a longitudinal axis of a distal handle portion parallel to and separate from a longitudinal axis of a proximal handle portion. In some embodiments, a longitudinal axis of a distal handle portion is offset from a longitudinal axis of a proximal handle portion.

Accordingly, pursuant to one aspect, there is provided a surgical instrument comprising a handle assembly comprising a proximal section, an intermediate section, and a distal section, the proximal section forming a first aperture and the distal section forming a second aperture, a tip assembly comprising a proximal end extending through the second aperture to a distal tip comprising an articulating portion, one or more control wires disposed internally to the handle assembly and the tip assembly and coupled to the articulating portion, an articulation control extending through the first aperture, the articulation control being actuatable between a plurality of positions to deflect the articulating portion, and one or more guides positioned internally in the handle assembly and operable to interact with the one or more control wires during actuation of the articulation control, wherein a first longitudinal axis of the proximal section of the handle assembly is offset from a second longitudinal axis of the distal section of the handle assembly.

Examples described herein may be further characterized by one or any combination of features, such as a Doppler probe is provided at the distal tip. In some examples, the articulating portion is a set of vertebrae. In some examples, the articulating portion is a segmented tube. In some examples, the articulation control is a roller wheel. In some examples, the roller wheel comprises a male protrusion on one side of a rotational axis and a female recess on the opposite side. In some examples, the housing assembly further comprises one or more of a spring tensioner, a fixed points system, an idler pulley, or biasing member. In some examples, the surgical instrument comprises one or more of a bone grasper, soft tissue grasper/dissector, scissors, flexible forceps, or a suction/irrigation line. In some examples, the housing assembly further comprises a second articulation control configured to operate the bone grasper, soft tissue grasper/dissector, scissors, the flexible forceps, or the suction/irrigation line. In some examples, the surgical instrument is a single-use, disposable device.

Pursuant to another aspect, an apparatus is provided. The apparatus comprises a manipulatable elongate member, comprising a set of individual vertebrae connected to form a distal portion of a tube, a continuous tube forming a proximal portion of the tube, and one or more pull wires configured to interconnect the set of individual vertebrae, a control handle assembly positioned at a proximal end of the manipulatable elongate member, wherein a first longitudinal axis of a proximal section of the control handle assembly is offset from a second longitudinal axis of a distal section of the control handle assembly, wherein the manipulatable elongate member is articulatable by actuating the one or more pull wires, wherein the control handle assembly is configured to manipulate the one or more pull wires.

Examples described herein may be further characterized by one or any combination of features, such as a Doppler probe is positioned at a distal tip. In some examples, the control handle assembly comprises at least one of a roller wheel, a thumb control, and a spring bias. In some examples, the control handle assembly comprises one or more posts operable to create tension on the one or more pull wires. In some examples, the Doppler probe is an end-firing Doppler operable for detection in 360 degrees. In some examples, a layer of material is positioned outside the tube and forming a second tube. In some examples, one or more channels are positioned inside the tube. In some examples, at least one of a bone grasper, soft tissue grasper/dissector, scissors, a flexible forceps, or a suction/irrigation line is positioned in the one or more channels. In some examples, the set of individual vertebrae are formed by at least one of hinging and molding. In some examples, a vertebra is positioned at a proximal end of the set of individual vertebrae is configured with a lip for engagement with the continuous tube.

Pursuant to another aspect, an apparatus is provided. The apparatus comprises a manipulatable elongate member, comprising a set of individual vertebrae connected to form a distal portion of a tube, a continuous tube forming a proximal portion of the tube, and one or more rods configured to interconnect the set of individual vertebrae, a control handle assembly positioned at a proximal end of the manipulatable elongate member, wherein a first longitudinal axis of a proximal section of the control handle assembly is offset from a second longitudinal axis of a distal section of the control handle assembly, wherein the manipulatable elongate member is articulatable by actuating the one or more rods.

Examples described herein may be further characterized by one or any combination of features, such as the one or more rods are configured to push and pull the set of individual vertebrae and produce articulation at a distal tip of the manipulatable elongate member. In some examples, each of the set of vertebrae form at least one tapered edge. In some examples, the tapered edge is cut at an angle of 20 degrees or less from a plane along a transverse axis. In some examples, the tapered edge forms an angled plane offset from a center of the radial axis.

Further aspects, advantages and areas of applicability will become apparent from the description provided herein. The description and specific examples are intended for purposes of illustration only and are not intended to limit the scope of the present disclosure.

DESCRIPTION OF THE DRAWINGS

The drawings described herein are for illustration purposes only and are not intended to limit the scope of the present disclosure in any way.

Figure 1:
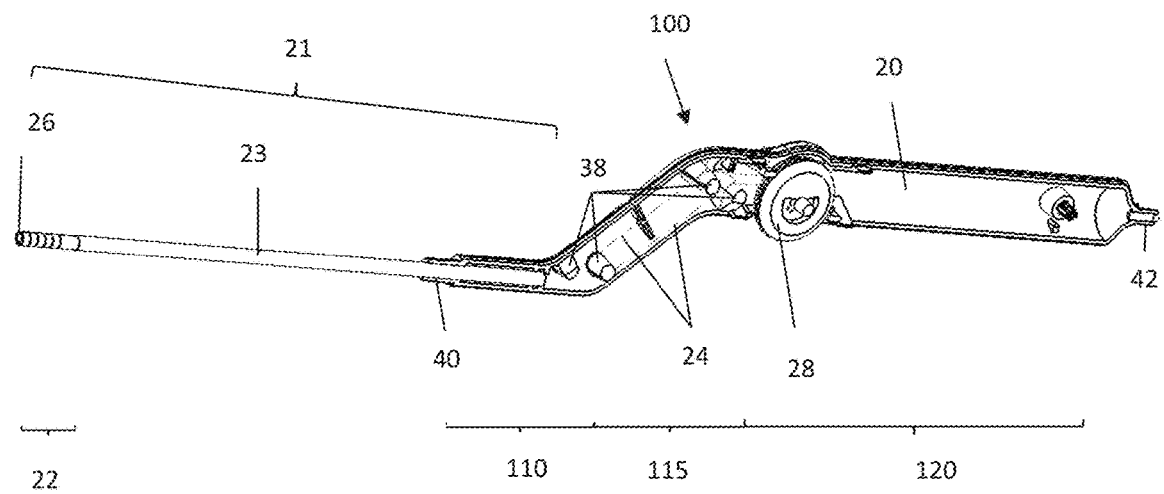
FIG. 1 illustrates a perspective view of an interior of a handle assembly, in accordance with some embodiments of the disclosure.
Figure 2A:
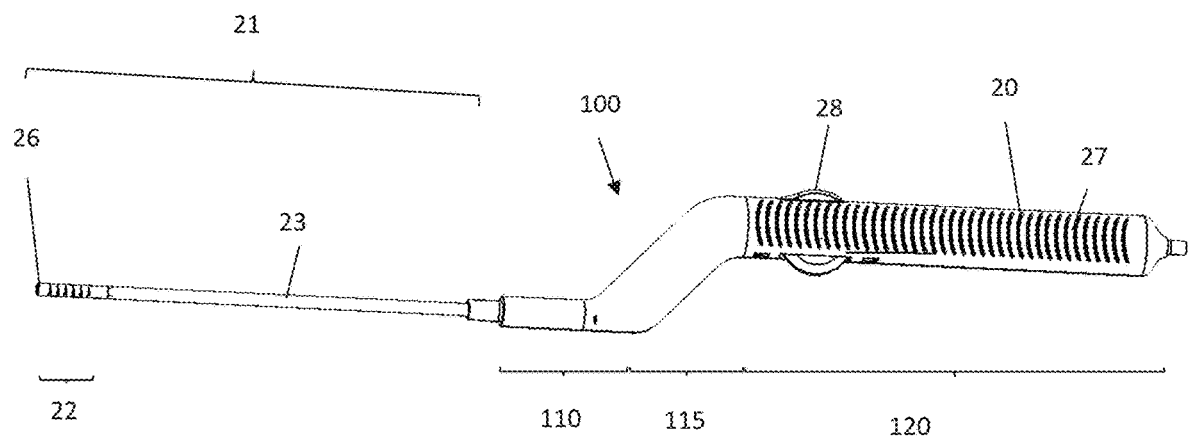
FIG. 2A illustrates a left side view of a handle assembly, in accordance with some embodiments of the disclosure.
Figure 2B:
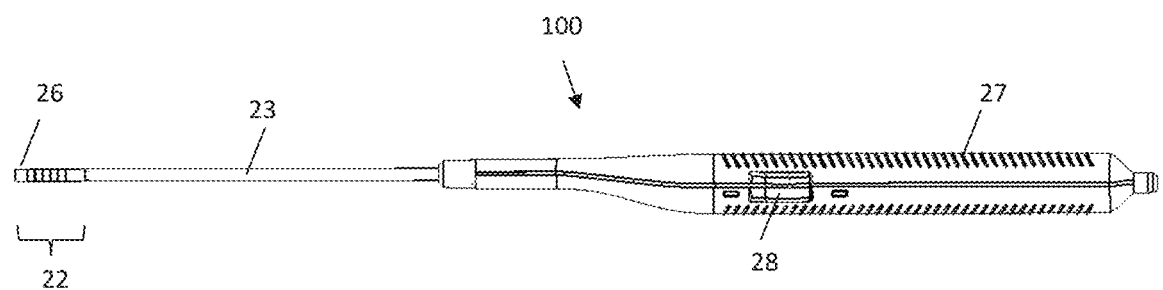
FIG. 2B illustrates a top view of a handle assembly, in accordance with some embodiments of the disclosure.
Figure 2C:
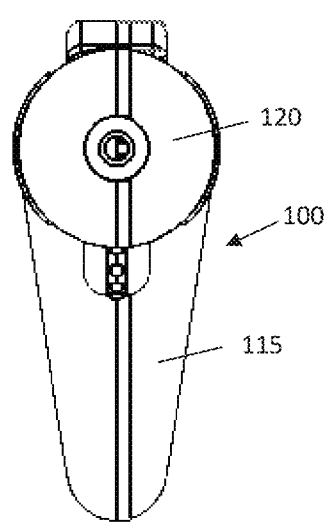
FIG. 2C illustrates a rear view of a handle assembly, in accordance with some embodiments of the disclosure.
Figure 2D:
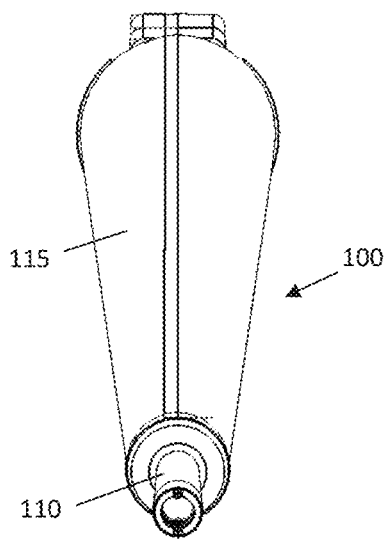
FIG. 2D illustrates a front view of a handle assembly, in accordance with some embodiments of the disclosure.

These and other features of the present embodiments will be understood better by reading the following detailed description, taken together with the figures herein described. The accompanying drawings are not intended to be drawn to scale. For purposes of clarity, not every component may be labeled in every drawing.

DETAILED DESCRIPTION

An articulating microsurgical instrument is disclosed herein. A handle assembly enables a user to hold the device and articulate a distal tip portion. The handle assembly may include an offset between a distal handle portion and a proximal handle portion, or bayonet shape, to provide a clear line of site between the user's point of view and the point of entry, without the obstruction of a user's extremities. The handle assembly may include a longitudinal axis of a distal handle portion being parallel to and separate from a longitudinal axis of a proximal handle portion. In some embodiments, the handle assembly may be a straight handle, where the distal handle portion and the proximal handle portion extend along a single axis. In some embodiments, the straight handle may include a set of posts. The handle may be of a round profile, optionally with an embossed or debossed texture on an outer surface to help the user operate, rotate, and move axially with steady precision. The handle assembly may house mechanisms and elements for guiding both movable and permanently stationary parts. In some embodiments, the handle assembly may be 3 cm or less, 2.5 cm or less, or 1.5 cm or less in outer diameter. In some embodiments, the handle assembly may include an inner lumen with a diameter of at least 1.2 cm, at least 1.5 cm, or at least 2.0 cm. Other alternatives for the size of the handle assembly and inner lumen are contemplated.

The articulating microsurgical instrument may be configured as a single-use, disposable device. It is desirable to provide a single-use, disposable device as single-use devices minimize the risk of cross-contamination that can be related to the use of devices that are re-sterilized. This is particularly important with devices that contain hard to clean components or mechanisms, such as a microsurgical articulating tip. Providing a disposable device allows for the use of materials that would not necessarily need to be of a type that would be appropriate for re-sterilization procedures following use, which could potentially decrease material costs of the device. This is especially important in the current era of cost containment prevalent within the healthcare industry. It is desirable to provide a single-use disposable device such that all components are provided in a simple packaging ready to go for a given procedure type. The articulating microsurgical instrument may be configured for use with a diagnostic sensing instrument positioned at a distal end. In some embodiments, the diagnostic sensing instrument may be configured as a Doppler probe at a distal end. The articulating microsurgical instrument may be configured for manipulating a distal end to detect the position of one or more vessels during a surgical procedure. The articulating microsurgical instrument may be configured for detection of the carotid artery during endonasal surgeries such as, for example, pituitary surgeries.

It is desirable for a user to be provided with the ability to articulate the angle of the Doppler probe at a distal tip as the angle of insonation may be significant in providing detection of critical arteries. In some embodiments, an end-firing Doppler is provided. The end-firing Doppler may be configured for 360-degree detection. In some embodiments, 360-degree detection may be achieved via deflection in two opposite directions. For example, 360 degree detection may be achieved via a first deflection of the distal tip of the instrument of up to 180 degrees in one direction from the longitudinal axis of the instrument to a fully curved position and via a second deflection of the distal tip of the instrument of up to 180 degrees in a direction opposite the first direction to a second fully curved position opposite the first fully curved position. In some embodiments, 360-degree detection may be achieved via rotation of a user's hand.

In other embodiments, the articulating microsurgical instrument may include a bone grasper, soft tissue grasper/ dissector, scissors, flexible forceps, or a suction/irrigation line. It is desirable for a user to be provided with the ability to manipulate an angle of a bone grasper, soft tissue grasper/ dissector, scissors, flexible forceps, or a suction/irrigation line for targeting the angle of cutting, grasping or suction/ irrigation and/or conducting a surgical procedure in a more effective and efficient manner. It is desirable for a user to be able to reach difficult locations and manipulate around anatomical regions as needed during a procedure.

The one or more control wires may be manipulated by a user using a rotating body or a slide trigger. In some embodiments, the rotating body may be a rotating wheel. In some embodiments, spiral guides are not required to surround the one or more control wires. Thus, the control wires may float in the handle assembly and may be guided by a spring tensioner, fixed points system, an idler pulley, or biasing member. The handle assembly may additionally contain one or more pulley tracks or spools to guide the control wire through the handle assembly. The spring tensioner, fixed points system, or idler pulley may be used for transferring force through the rotating wheel or slide trigger to cause bending at a distal tip. In some embodiments, a set of individual vertebrae are positioned inside the distal tip.

Figure 5A:
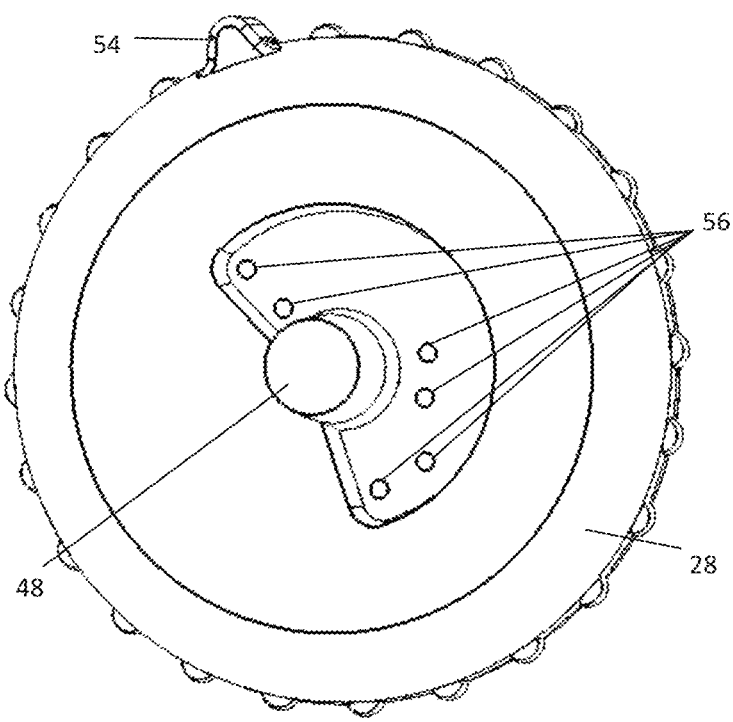
FIG. 5A illustrates a left side view of a roller wheel, in accordance with some embodiments of the disclosure.
Figure 5B:
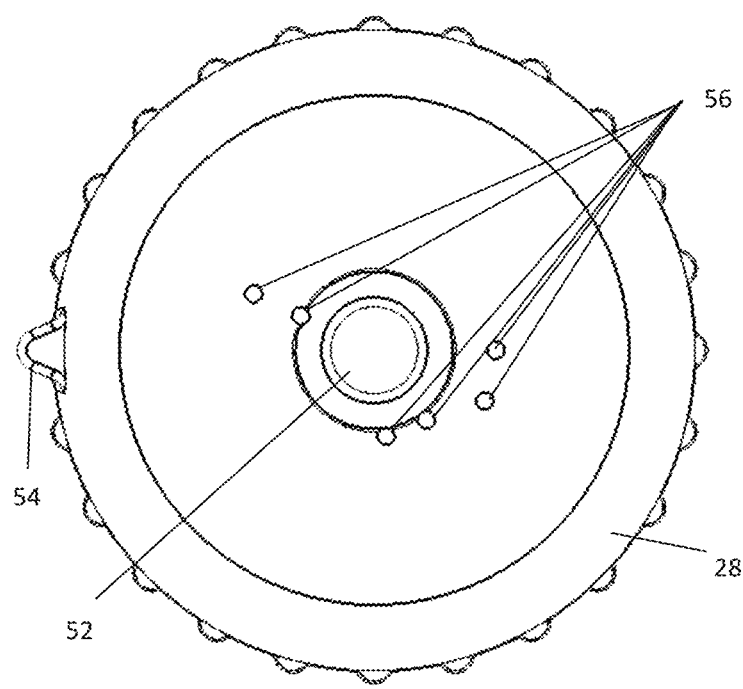
FIG. 5B illustrates a right side view of a roller wheel, in accordance with some embodiments of the disclosure.
Figure 5C:
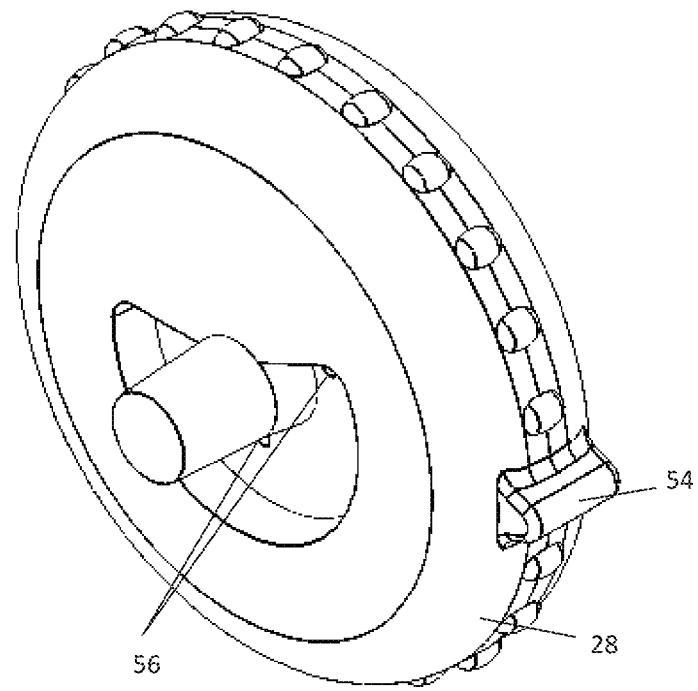
FIG. 5C illustrates left perspective view of a roller wheel, in accordance with some embodiments of the disclosure.

Turning now to the drawings to illustrate example embodiments of the present teachings, FIG. 1 details one embodiment of the disclosure wherein one or more control wires 24 may be housed inside handle assembly 20. Handle assembly 20 enables a user to hold articulating microsurgical instrument 100 and articulate distal tip 26. FIG. 1 details handle assembly 20 as including a longitudinal axis of a distal handle portion 110 being parallel to and separate from a longitudinal axis of a proximal handle portion 120. An intermediate handle portion 115 connects distal handle portion 110 to proximal handle portion 120. In the illustrated embodiment, handle 20 has a round profile and is provided with a textured surface 27. Handle assembly 20 is illustrated as including a pair of control wires 24 which rest against a set of posts 38. One or more posts 38 may be one or more guides. Posts 38 are configured to act as guides for control wires 24 as they are manipulated back and forth using the articulating mechanism (roller wheel 28, in the embodiment illustrated in FIG. 1). Roller wheel 28 may contain one or more fixation points 56, as illustrated in FIGS. 5A-C, for securing the ends of control wires 24 to roller wheel 28. Fixation points 56 may be wedges or slots used to affix the ends of control wires 24.

The radial and/or longitudinal position of posts 38 or fixation points 56 may correspond with the amount of travel, dictated by the geometry of tip assembly 21, such that little or no slack is introduced in the control wires 24 upon articulating, especially in the case of two or more control wires 24 for control of multiple directions of movement of distal tip 26. Such a configuration would provide for rigidly holding the articulation position in two (or more) directions. The exact positioning of posts 38 or fixation points 56 may also be optimized for the natural comfortable travel distance of human extremities. For example, posts 38 and/or fixation points 56 where control wire 24 is secured to roller wheel 28 may be adjusted to limit rotational requirements of roller wheel 28 for user comfort. In another embodiment, travel of control wire 24 is augmented by additional pulleys, springs, cams, or gears within handle assembly 20. In some embodiments, control wire 24 may be wrapped around the roller wheel 28 one or more times and secured with cyanoacrylate and/or other adhesives.

Figure 18:
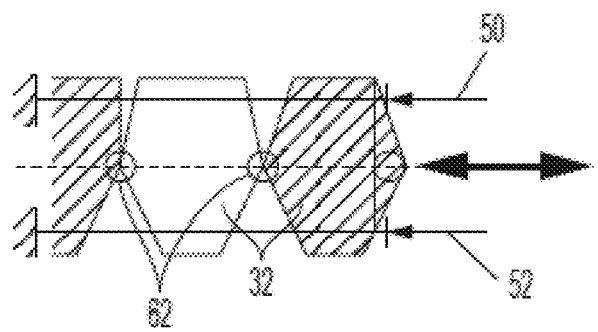
FIG. 18 illustrates hinged vertebrae of a tip assembly, in accordance with some embodiments of the disclosure.
Figure 19:
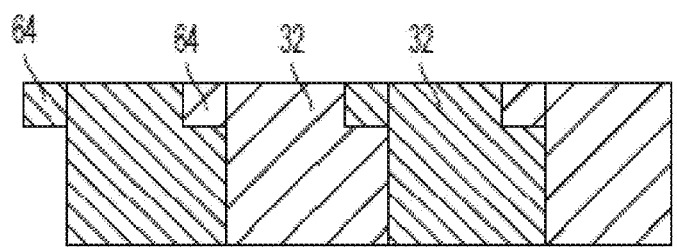
FIG. 19 illustrates vertebrae of a tip assembly connected using keyway features, in accordance with some embodiments of the disclosure.

In some embodiments, alternative mechanisms may be employed for effecting articulation of distal tip 26. For example, a rigid elongated body may be manipulated to effect articulation. Rigid elongated body may be pushed and pulled or rotated within the housing to articulate distal tip 26. Alternatively, articulation may be achieved through relative adjustment of fixation point positions. For example, as illustrated in FIG. 18, one or more cam bodies may interface with one or more hinged tip pieces (vertebrae 32). As shown in FIG. 18, hinges 62 are used to interconnect individual vertebrae 32. In some embodiments, one or more elongate members may be included that push and/or pull on hinged tip pieces (vertebrae 32) in different places in order to effect articulation. FIG. 19 illustrates an example embodiment wherein flats or keyway features 64 are provided on vertebrae 32 and are configured to provide alignment between individual vertebrae 32 both during assembly and during use.

In some embodiments, articulating portion 22 comprises a set of individual vertebrae 32. Some example vertebrae 32 are shown in FIGS. 8A-10C. Each vertebra 32 may be provided with a protruded portion 35 in an upper portion of vertebra 32 to allow distal tip 26 to bend as the one or more control wires are actuated. Protruded portion 35 may be an angled top edge, a flat top edge, or a curved top portion that protrudes further than an adjacent lower portion of vertebra 32. Control wires may be routed through holes in the vertebrae 32 and fixed at a distal tip 26.

Figure 13:
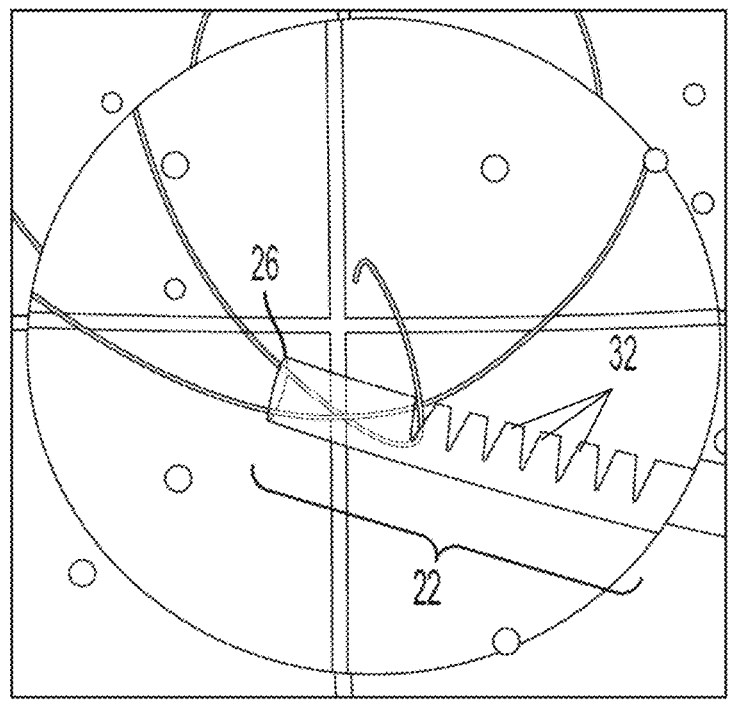
FIG. 13 illustrates an example of a distal tip showing vertebrae cut from a pebax tube, in accordance with some embodiments of the disclosure.

In some embodiments, articulating portion 22 comprises a single lumen tube. In some embodiments, articulating portion 22 may include a segmented tube, for example as shown in FIG. 13.

An outer diameter of the tip shaft may be approximately 5 mm or less, 4 mm or less, or 3 mm or less. The distal tip 26 may be configured to remain at its articulated angle as a set point until further actuation of the trigger. The distal tip 26 articulating portion may be approximately 0.5" to 0.75" long with a flexible covering.

One side of an optionally two-part handle shell assembly, shown in FIGS. 1-4C, may contain some or most of the guides for the components housed within the device. In such an embodiment, the method of assembly is simplified, as articulation and initial function-testing can occur before fully enclosing the device shell. In one embodiment, control wires are guided by extruded posts, and a Doppler wire is guided by yokes, holding it in place regardless of orientationally-dependent gravitational force or other outside forces.

An additional part of a handle shell may serve to enclose and further guide internal components. In one embodiment, a second half of a two-part handle shell contains transverse extruded guiding features that hold one or more control wires in a particular axial position and prevent said control wires from sliding off of complementary guide features such as posts 38.

Figure 17:
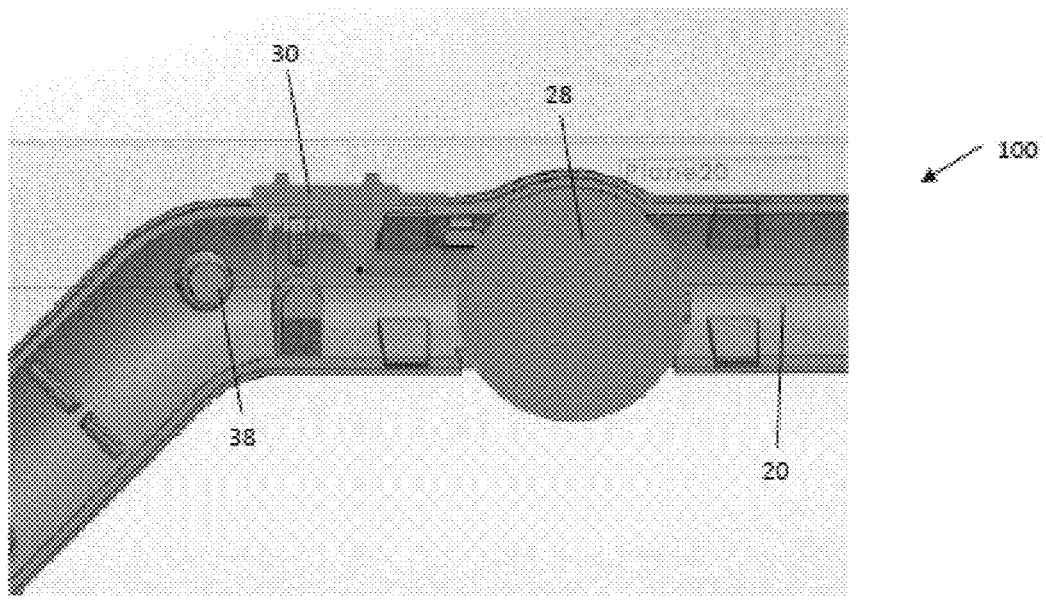
FIG. 17 illustrates a rear handle portion showing a slide trigger and wheel for manipulating a surgical tool as well as a tip of the articulating microsurgical instrument, in accordance with some embodiments of the disclosure.

The handle assembly 20 contains an articulation control. In some embodiments, the articulation control is actuated with a single finger of a user. In some embodiments, articulation control is a mechanism controlled by a palm squeeze, a hand twist, or a wrist control. In some embodiments, articulation control is a roller wheel 28. In some embodiments, articulation control is a slide trigger 30. FIG. 17 illustrates one embodiment which includes slide trigger 30 as well as roller wheel 28. Embodiments with more than one control mechanism may be configured to manipulate or operate a surgical tool in addition to control of articulation at a distal tip. For example, slide trigger 30 may control one of manipulation or operation of a surgical tool while roller wheel 28 may control articulation of a distal tip. Alternatively, slide trigger 30 may control articulation of a distal tip while roller wheel 28 may control one of manipulation or operation of a surgical tool.

Figure 3A:
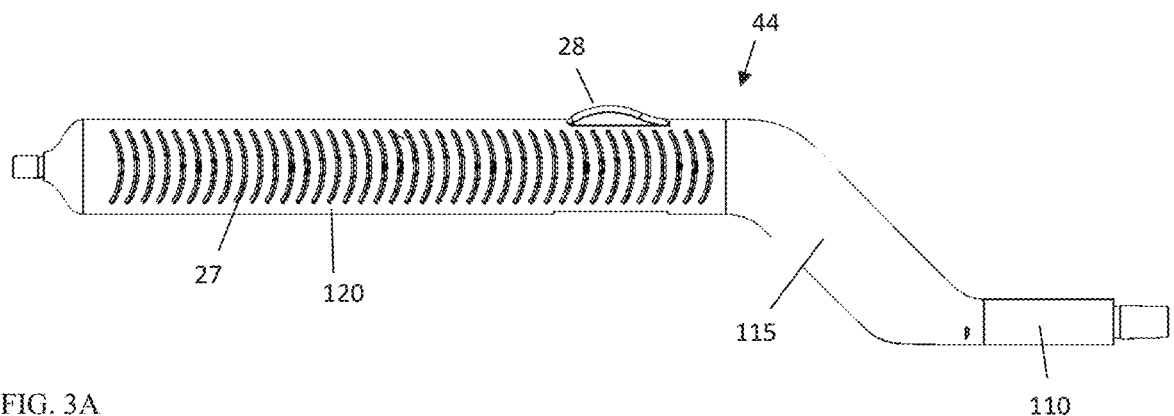
FIG. 3A illustrates a right side view of a right handle housing portion, in accordance with some embodiments of the disclosure.
Figure 3B:
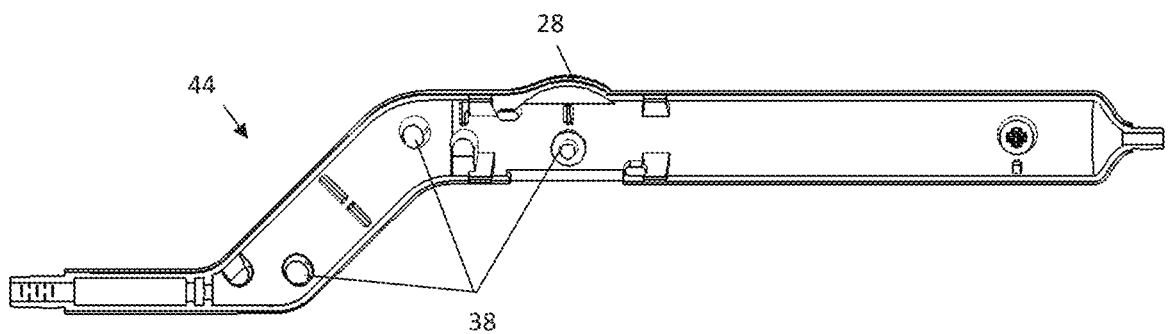
FIG. 3B illustrates a left side view of a right handle housing portion, in accordance with some embodiments of the disclosure.
Figure 3C:
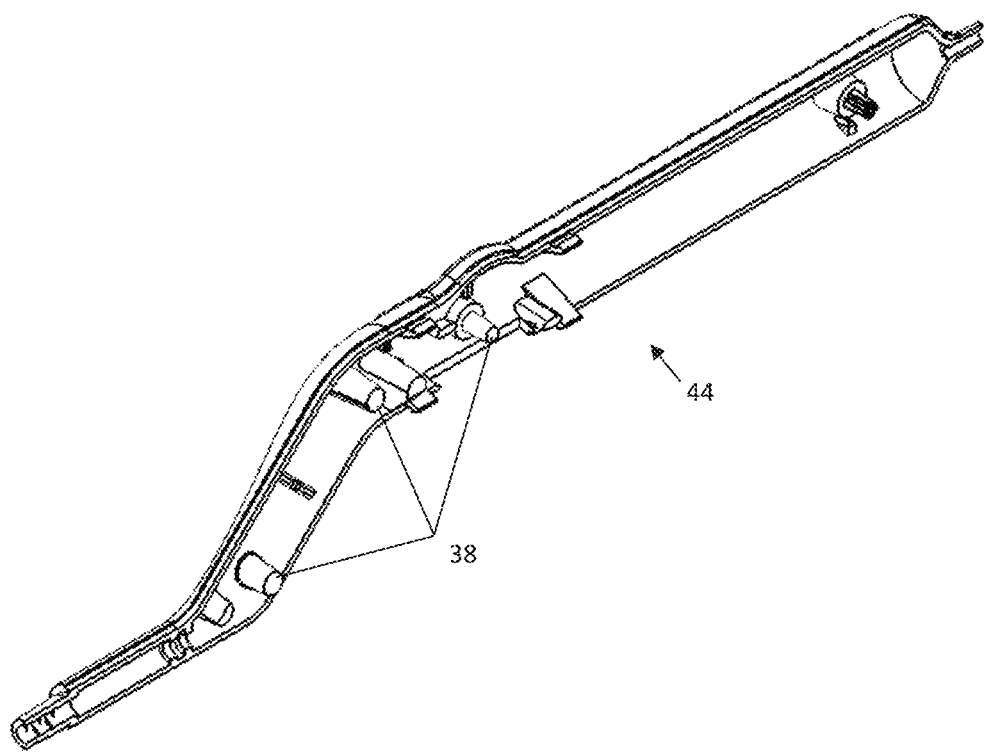
FIG. 3C illustrates a top right perspective view of a right handle housing portion, in accordance with some embodiments of the disclosure.
Figure 4A:
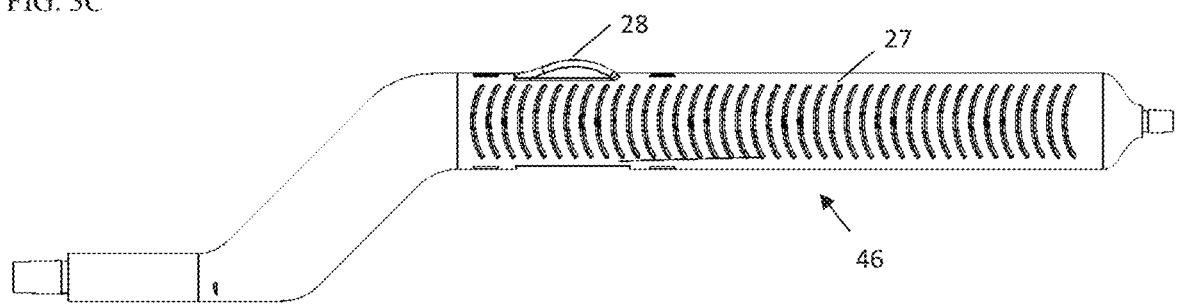
FIG. 4A illustrates a left side view of a left handle housing portion, in accordance with some embodiments of the disclosure.
Figure 4B:
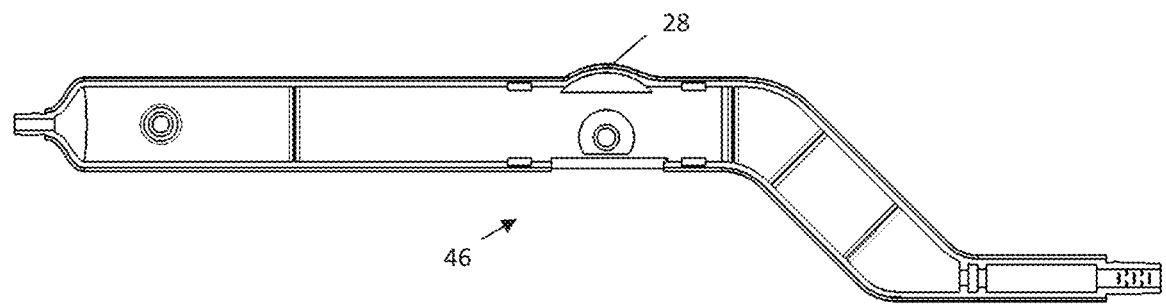
FIG. 4B illustrates a right side view of a left handle housing portion, in accordance with some embodiments of the disclosure.
Figure 4C:
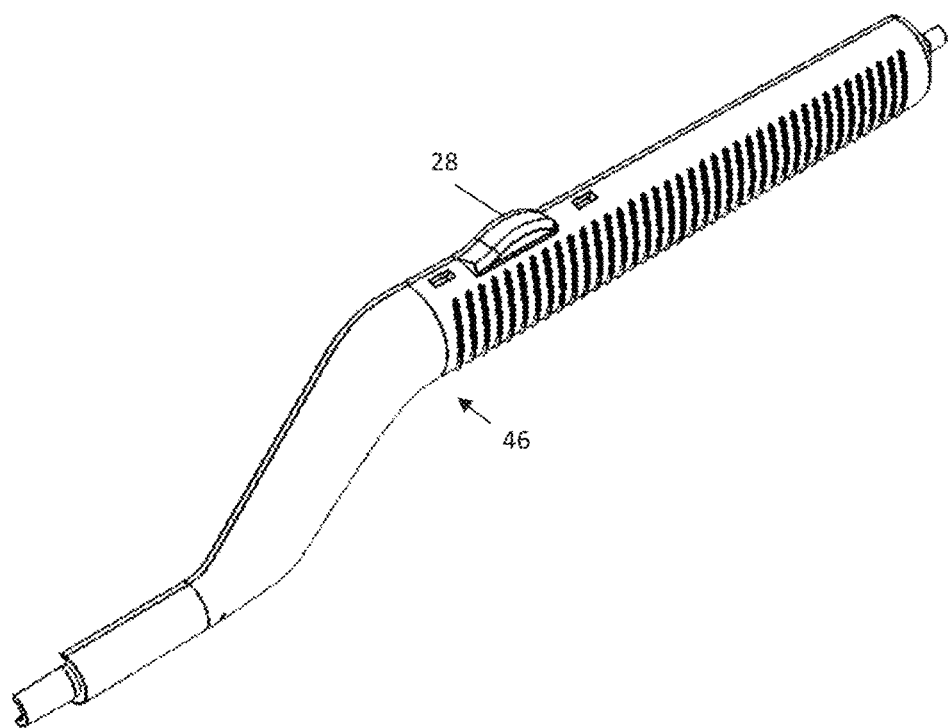
FIG. 4C illustrates top left perspective view of a left handle housing portion, in accordance with some embodiments of the disclosure.

Roller wheel 28 is illustrated in FIGS. 1-2B and 3A-5C. Roller wheel 28 may include one or more male/female interfaces 48, 52 configured to constrain an axis of rotation. FIGS. 3A-3C illustrate a first half clamshell 44 and FIGS. 4A-4C illustrate a second half clamshell 46. First half clamshell and second half clamshell are configured to snap together to form handle assembly 20. FIGS. 5A-C illustrate one embodiment of roller wheel 28 in which a male protrusion 48 is positioned on one side of the rotational axis and a female recess 52 is positioned on the other side. Such combination allows for increased mated axis length, beyond the center point of roller wheel 28. The corresponding male protrusion 48 of roller wheel 28 results in greater stability both during and after assembly once the complementary handle shell is in place. The rotating mechanism, or roller wheel 28, may include a recess or cavity to house fasteners, knots, or adhesives. This recess or cavity, as well as an optional proud feature and an optional augmentation of soft material at the interface of the roller wheel 28 and one of its mating parts, may be integrated or added as a brake to counteract the elastic forces from the tip and/or Doppler probe, resulting in positional stability without the necessity of constant user-applied force on the trigger. For example, a shoulder 54 may be provided, as shown in FIGS. 5A-5C, around the axis on the handle or wheel that is used to optimize the pressure and braking force of the interface between the roller wheel and the handle. The roller wheel 28 may contain one or more holes or fixation points 56 for securing the proximal end of a control wire 24.

Figure 6A:
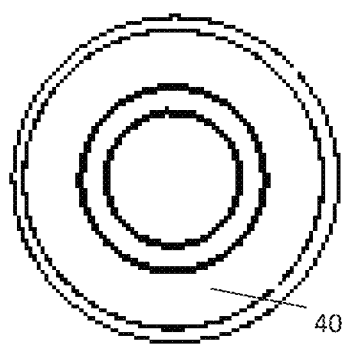
FIG. 6A illustrates a front view of a distal cap, in accordance with some embodiments of the disclosure.
Figure 6B:
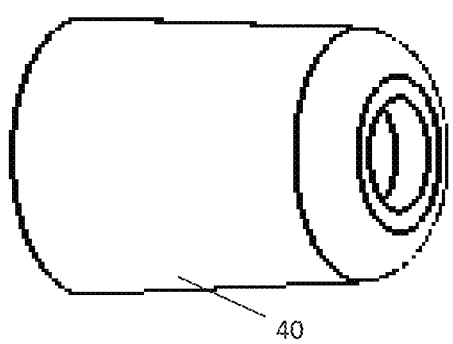
FIG. 6B illustrates a perspective view of a distal cap, in accordance with some embodiments of the disclosure.

A cap 40, 42 may be provided at a distal end of the handle, as shown in FIGS. 6A-B. In some embodiments, the distal cap 40 may be configured with an annular snap-fit, may be threaded, and/or bonded. The distal cap 40 may be configured to constrain the shaft radially, and optionally axially.

Figure 7A:
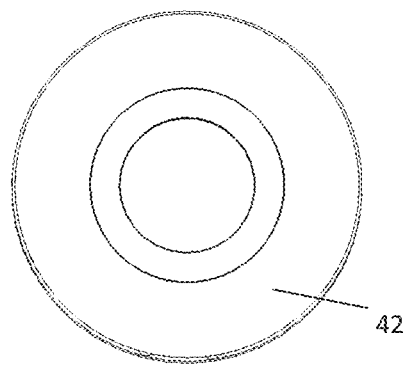
FIG. 7A illustrates a rear view of a proximal cap, in accordance with some embodiments of the disclosure.
Figure 7B:
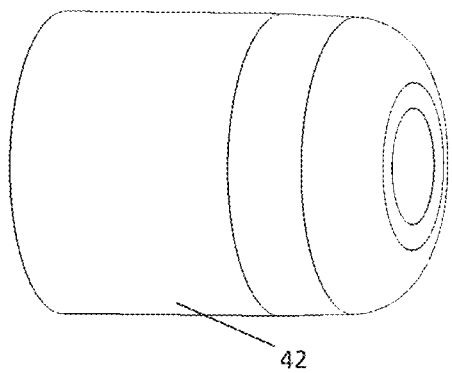
FIG. 7B illustrates a perspective view of a proximal cap, in accordance with some embodiments of the disclosure.
Figure 8A:
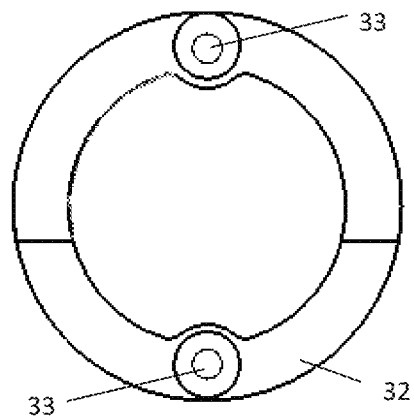
FIG. 8A illustrates a cross-sectional view of a vertebra that may comprise a portion of a tip assembly, in accordance with some embodiments of the disclosure.
Figure 8B:
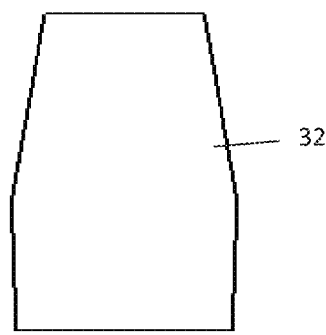
FIG. 8B illustrates a side view of a vertebra that may comprise a portion of a tip assembly, in accordance with some embodiments of the disclosure.
Figure 8C:
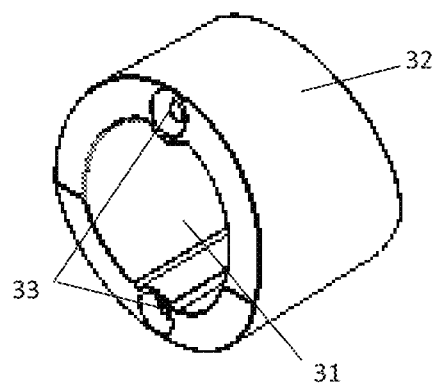
FIG. 8C illustrates a perspective view of a vertebra that may comprise a portion of a tip assembly, in accordance with some embodiments of the disclosure.
Figure 9A:
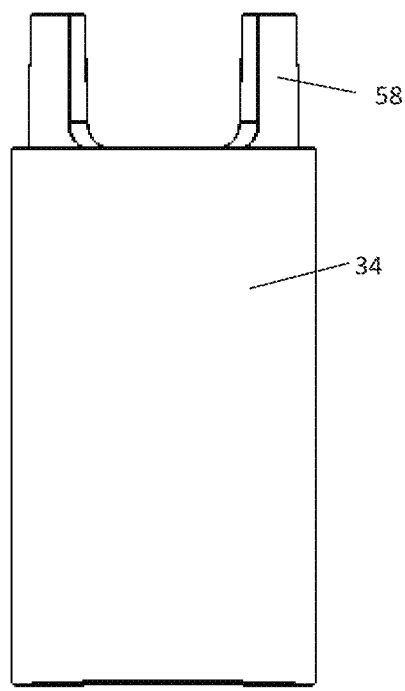
FIG. 9A illustrates a top view of a proximal-most vertebra that may comprise a portion of the tip assembly, in accordance with some embodiments of the disclosure.
Figure 9B:
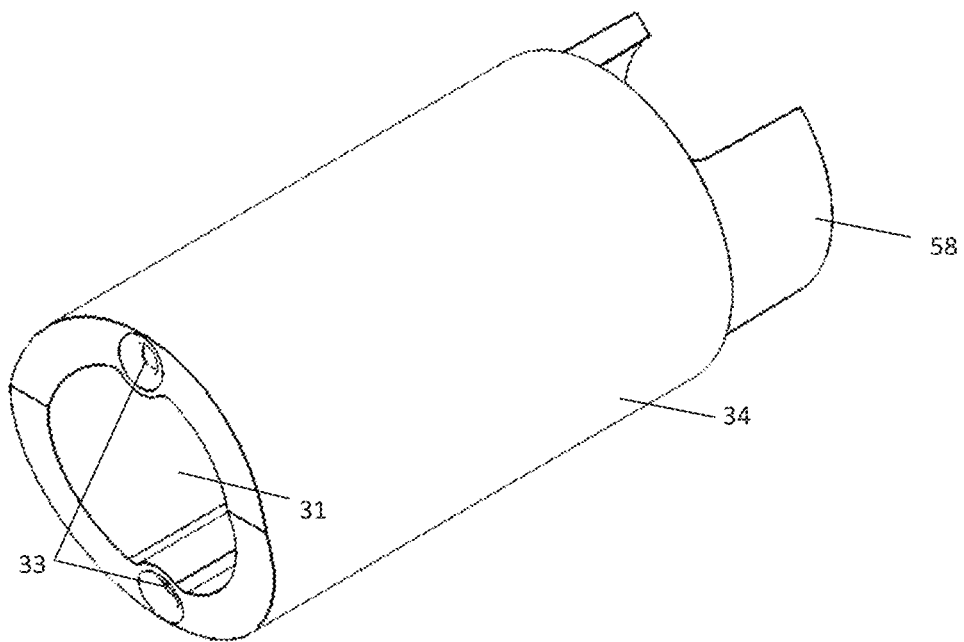
FIG. 9B illustrates a perspective view of a proximal-most vertebra that may comprise a portion of the tip assembly, in accordance with some embodiments of the disclosure.
Figure 9C:
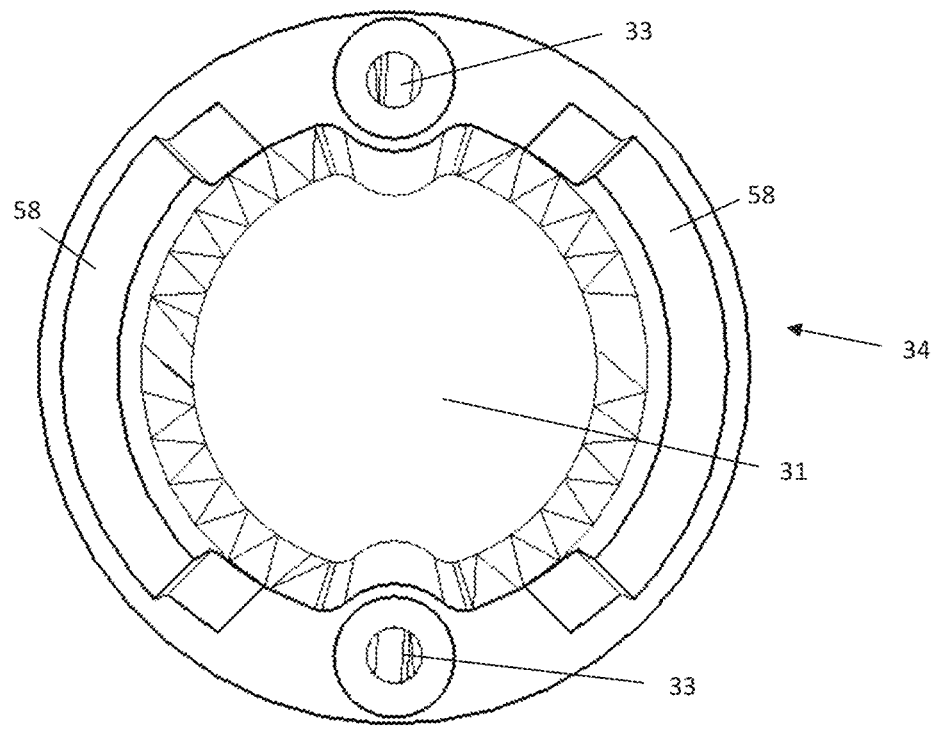
FIG. 9C illustrates a cross-sectional view of a proximal-most vertebra that may comprise a portion of the tip assembly, in accordance with some embodiments of the disclosure.
Figure 9D:
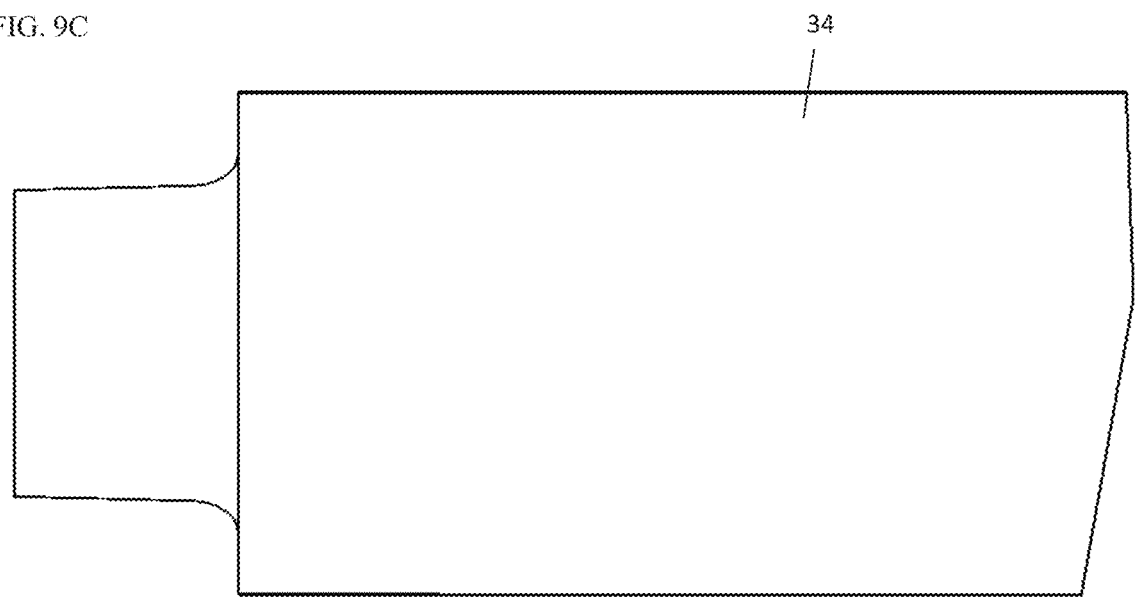
FIG. 9D illustrates a side view of a proximal-most vertebra that may comprise a portion of the tip assembly, in accordance with some embodiments of the disclosure.

A proximal cap 42 may be provided at a proximal end of the handle, as shown in FIGS. 7A-B. In some embodiments, the proximal cap 42 may be configured with an annular snap-fit, may be threaded, and/or bonded. The proximal cap 42 may be configured to constrain a Doppler probe cable, or any other part that must exit the proximal direction, radially, and optionally axially.

Articulating microsurgical instrument 100 may include a tip assembly 21 comprising an articulating portion 22 which is able to articulate or bend in one or more directions with an applied force from a user. In one embodiment, articulating portion 22 contains a proximal part, one or more middle parts, and a distal part. In an alternative embodiment, articulating portion 22 is comprised of a single body, such as is shown in FIG. 13, which may be configured to elastically deform to a predetermined desired position following actuation of an articulation control. In one embodiment, the articulating portion 22 is configured to articulate from 0 degrees, or straight, to 90 degrees, and back while under a predetermined load from internal components and/or outside forces. In other embodiments, articulating portion 22 may articulate between 0 degrees and 180 degrees in one direction and between 0 and 180 degrees in another direction. Various alternatives are contemplated. Modifications may be made to the tip geometry, tip material composition, and fixation points 56 of roller wheel 28 in an attempt to achieve proper articulation in both directions.

In one embodiment, articulating portion 22 comprises a multitude of segments. As shown for example in FIG. 8B, an example segment of articulating portion 22 is tapered 20 degrees from a plane along its transverse axis. One or more segments comprising articulating portion 22 may be tapered in this way. In one embodiment, there are equal tapers on each side of vertebra 32. In one embodiment, only one upper edge of vertebra 32 is tapered. In one embodiment, the angled plane is offset from the center of the radial axis. Offsetting the angled plane from the center of the radial axis removes more material from an upper portion of vertebra 32 and may result in a more mechanically advantaged articulation effect.

Some material elastic spring force may play a role in getting the tip back to straight, or zero degrees. The likelihood of rubbing or pinching of the tip cover sleeve 23 by the vertebra 32 may be mitigated by limiting the articulating angle between vertebra 32 and the corresponding maximum distance between vertebra 32. In addition to the primary angle taper, a cut-back taper may be introduced to compensate for insufficient mechanical advantage and material losses to get the tip back to straight, or zero degrees. In one embodiment, this cut-back is 2 degrees on each side of the vertebra 32, or 4 degrees including both sides. Vertebra 32 may include three lumens. Two side lumens 33 may be used for housing control wires 24, push/pull rods 50,52 for manipulating articulation in each direction, electrical cables to connect to the Doppler probe. In some embodiments, central lumen 31 may be configured to house one or more components (i.e. a Doppler probe, a bone grasper, soft tissue grasper/dissector, scissors, flexible forceps, or a suction/irrigation line). In some embodiments, one or more components (i.e. a Doppler probe, a bone grasper, soft tissue grasper/dissector, scissors, flexible forceps, or a suction/irrigation line) may be integrated into the housing and electrical and/or control wires may be positioned within one or more of side lumen 33. Vertebra 32 are optionally two-lumen, with one side lumen 33 housing a control wire 24 and/or an electrical wire for Doppler probe and one central lumen 31 housing one or more housed components.

In some embodiments, a proximal-most vertebra 34 may be different from the middle vertebra 32. One example embodiment of proximal-most vertebra is shown in FIGS. 9A-9D. The proximal-most vertebra may have an angled taper on one side of its main radial axis, and no angled taper on the other side, so it may fit flush against a shaft at a proximal end of articulating portion 22. The proximal-most vertebra 34 optionally includes one or more proximal protrusion guides 58, or lip, to act as a guiding concentric interface to the shaft, especially if the shaft is single-lumen. The proximal-most vertebra 34 may comprise two or three lumens 31, 33.

Figure 10A:
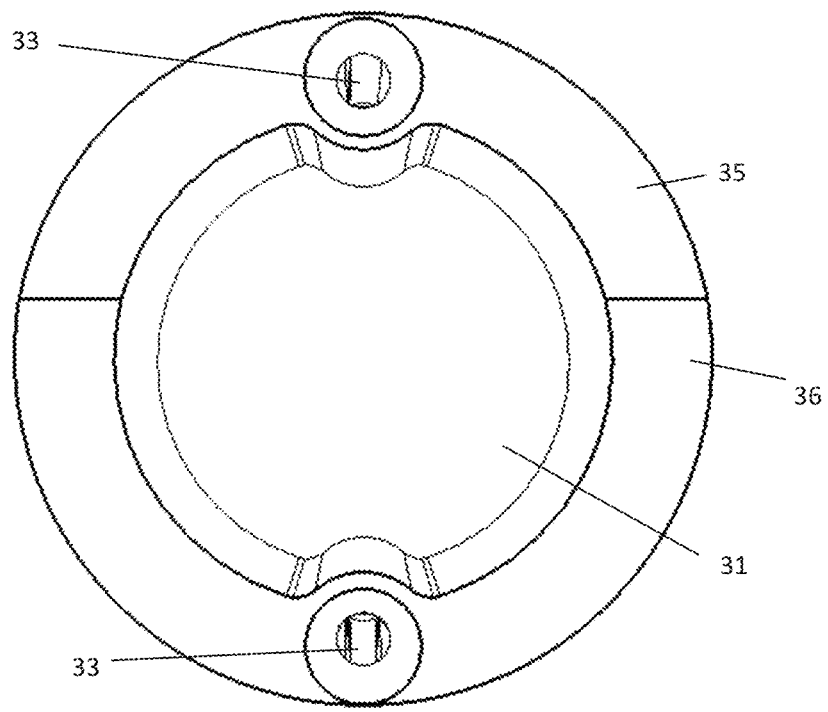
FIG. 10A illustrates a cross-sectional view of a distal-most vertebra that may comprise a portion of the tip assembly, in accordance with some embodiments of the disclosure.
Figure 10B:
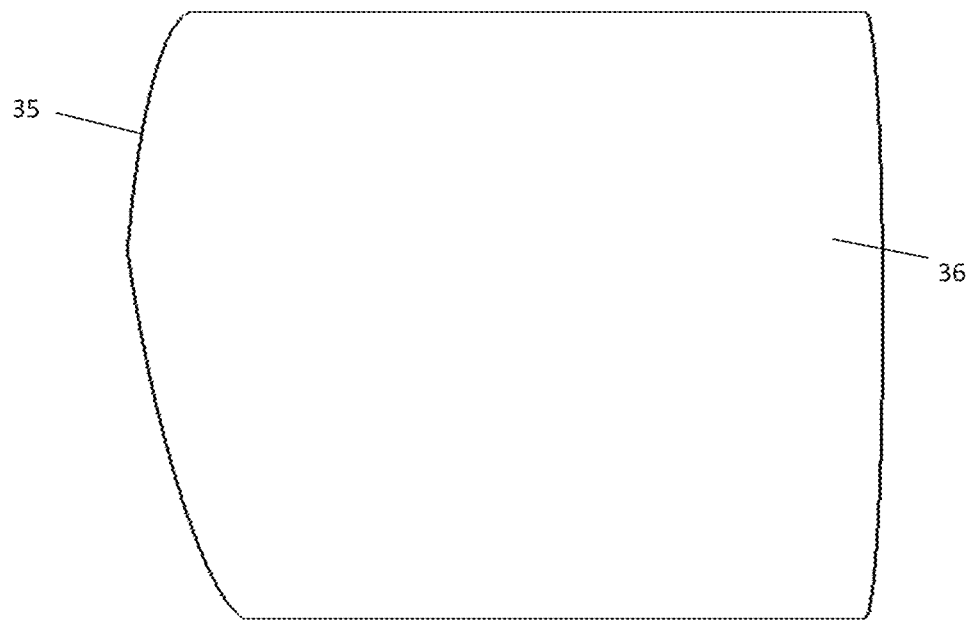
FIG. 10B illustrates a side view of a distal-most vertebra that may comprise a portion of the tip assembly, in accordance with some embodiments of the disclosure.
Figure 10C:
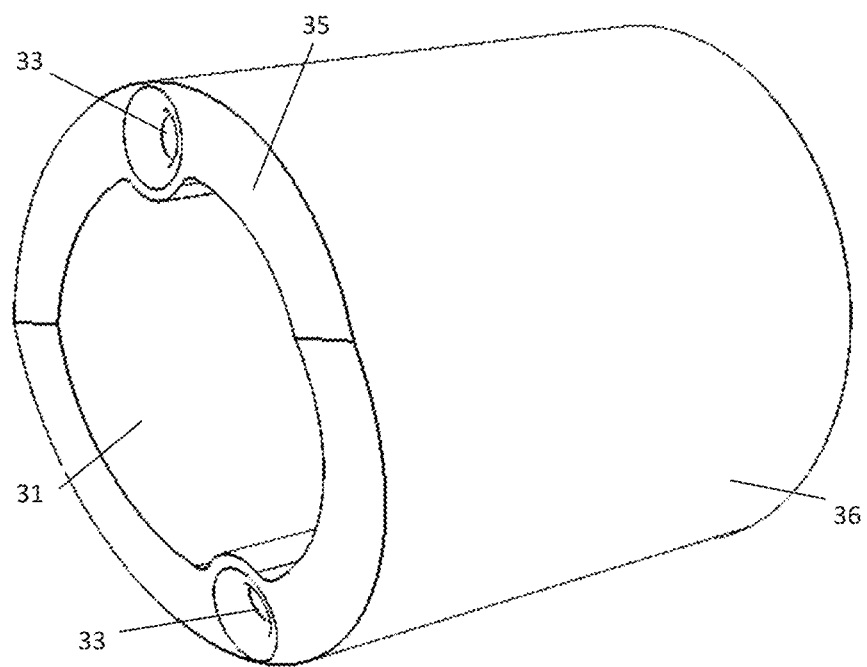
FIG. 10C illustrates a perspective view of a distal-most vertebra that may comprise a portion of the tip assembly, in accordance with some embodiments of the disclosure.

In some embodiments, a distal-most vertebra 36 may be different from the middle vertebrae. One example embodiment of distal-most vertebra 36 is shown in FIGS. 10A-C. The distal-most vertebra 36 may have an angled taper on the proximal side of its main axis to contribute to articulation effect, and no angled taper on the distal side to provide an orthogonal interface for the encompassed component(s). The distal-most vertebra 36 may be longer than the other pieces so as to provide better reach within the body upon articulation. The distal-most vertebra 36 may comprise two or three lumens 31, 33.

In one aspect, an outer sleeve 23 may be added to tip assembly 21 to keep pinch points and control wires from coming into contact with human tissue. In some embodiments, outer sleeve 23 is a soft tip cover sleeve. In one embodiment, outer sleeve 23 is made from thin-wall (0.003") polyether block amide. In another embodiment, outer sleeve 23 is made from polytetrafluoroethylene. In another embodiment, outer sleeve 23 is made from polyurethane. In another embodiment, outer sleeve 23 may comprise heat shrink tubing or flat ribbon with adhesive. The elastic spring force of the outer sleeve 23 may be leveraged to assist the tip in getting back to a straight configuration, or alternatively, it may be minimized by selecting more compliant materials with thinner walls.

A single lumen or a multi-lumen shaft may be used. Single lumen shafts generally have the benefit of simplicity and lower cost. Multi-lumen shafts generally have the benefit of repeatable assembly. In one embodiment, a single lumen shaft is made from a high elastic modulus polymer such as PEEK or polyimide. Alternatively, a stainless steel single lumen shaft may be used to achieve a thin-wall and maximum space on the inside and outside.

One or more control wires 24 may be used to articulate the tip. Control wires 24 are optionally made from metal, or alternatively made from polymers. In one embodiment, control wire 24 is made from soft stainless steel wire, which easily bends and stays in position, but does not easily break or fail in tension. In some embodiments, control wire 24 is made from hardened stainless steel wire. In one embodiment, a hardened wire is used for the return wire and a soft wire is used for the articulation wire. In another embodiment, control wire 24 is made of nylon, which may be of toughened or film-based variety. In another embodiment, control wire 24 is made from polyester liquid crystal polymer fibers. In another embodiment, control wire 24 is made from a nickel titanium alloy. In some embodiments, control wire 24 is made from ePTFE or LCP monofilament. In some embodiments, control wire 24 is annealed in one area or along the full length for optimizing the elastic modulus for specific areas.

Figures 11A, 11B:
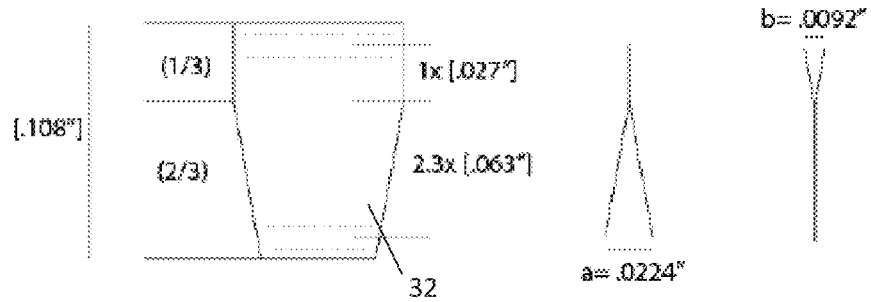
FIG. 11A illustrates geometry of an example vertebra at a tip of an articulating microsurgical instrument in accordance with some embodiments of the disclosure.
FIG. 11B illustrates an example of a closed loop approach for control wire design with regard to tip geometry, in accordance with some embodiments of the disclosure.
Figure 12:
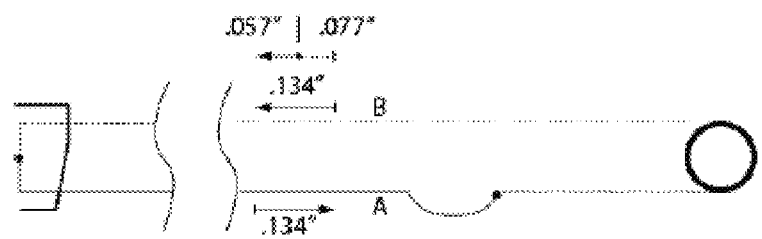
FIG. 12 illustrates an example of a closed loop approach for control wire design with regard to control wire travel distance, in accordance with some embodiments of the disclosure.

FIGS. 11A-12 show an analysis which explores the specific theoretical outcome of implementing a "closed loop" mechanism with a stationary idler. While this is referred to as a "closed loop" approach, there are two points of fixation along the loop, effectively resulting in two different lines. The A Line will refer to the line which must be pulled to articulate the tip toward 90 degrees, the B Line will refer to the line which must be pulled to get the tip back to straight (0 degrees). FIG. 11A illustrates geometry of an example vertebra at a tip of an articulating microsurgical instrument. Vertebra 32 is illustrated as having a total length of 0.108", with a straight portion having a length of 0.027" and an angled portion having a length of 0.063". FIG. 11B illustrates respective axial travel distance. FIG. 12 shows a closed loop configuration with maximum theoretical travel.

In FIG. 12, assuming the A Line is pulled 0.134", the theoretical maximum to reach full articulation with no deformation of the control wire 24 or the distal-most vertebra 36 or other vertebrae 32, the B Line is fed the 0.134" of wire. Of that amount, 0.057" is theoretically taken into the shaft/tip leaving 0.077" of line as loose slack.

With no deformation of the vertebrae 32, 36 or control wire 24, the tip should still get back to zero (straight) upon actuating the articulating mechanism back to a resting state. However, it may be mechanically disadvantaged, especially in the final portion of straightening, as the tip cover may be contributing less to the straightening effect.

Additionally, the slack in the B Line may result in allowed over-articulation of the tip with the influence of outside forces. For example, pulling the A Line 0.050" may theoretically bring the tip to 45 degrees and introduce ~0.029" of slack in the B Line. This amount of slack corresponds to about 61 degrees of angular play, meaning the tip angle may not be constrained from going all the way to 106 degrees, except for by the forces incurred by the tip cover. Slack may be minimized with biasing member acting as a tensioner. Slack may also be minimized through material selection, geometry, and fixed-point placement.

Laser cut polyether block amide may be used in the tip assembly 21, as shown for example in FIG. 13. The laser cut 63D polyether block amide vertebrae 32 are softer and more pliable than a hard plastic like ABS or PVC. For this reason, the vertebrae 32 may deform when subjected to forces applied by the control wires. If a control wire 24 starts to cut through a control lumen orifice wall, and the vertebrae 32 compress axially, then some of the work that is intended to articulate the tip is instead consumed by deforming the vertebrae 32, thereby resulting in a decreased actual articulation effect with a given stroke/pull length. Furthermore, upon articulating back to straight, or zero degrees, the B Line may be even further mechanically disadvantaged if the pivot points and lumen locations have been displaced or disfigured.

Figure 16:
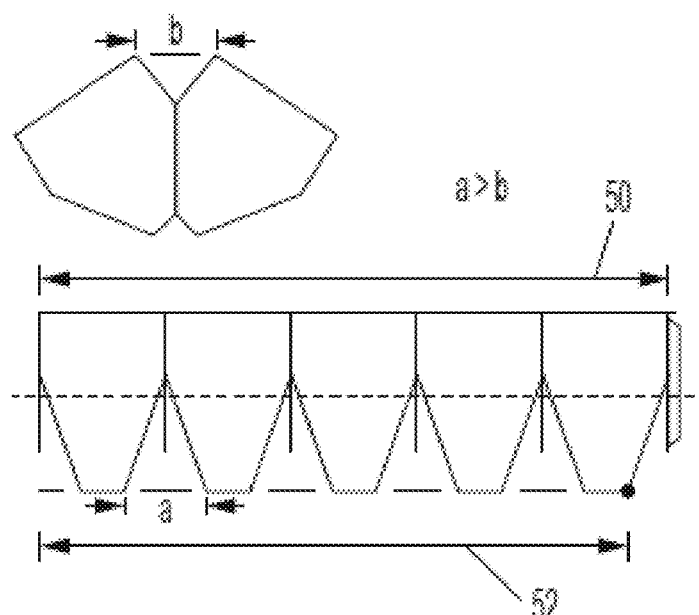
FIG. 16 illustrates a diagram illustrating rocking motion of a cross-section of a distal tip of an elongate member of an articulating microsurgical instrument, in accordance with some embodiments of the disclosure.

Nylon monofilaments stretch and undergo elastic deformation. There is a wide range of values for elongation at break of different nylons. Trilene XT is one example nylon. Assuming 15% Elongation at Break, if there are 6.0" of line between the distal end of the tip and the point of fixation on the roller wheel 28, that line would stretch 0.9" at the point of breaking. While the nylon monofilament isn't being loaded to the point of failure, even 20% of that amount (safety factor=5) would result in 0.180" of elongation, which is greater than the total amount of pull in the A Line that is theoretically needed to articulate fully. The neutral axis, or rocker point of the vertebra 32 must be moved toward the A Line control lumen so that the return (B) line has more mechanical advantage to get back to zero degrees. FIG. 16 illustrates an example embodiment showing vertebrae 32 rocking during articulation where separation a at rest becomes a smaller separation b during articulation. Tips should also include a harder material which will not yield or deform from the pressure of the control wire.

Figure 14:
FIG. 14 illustrates a cross-sectional view of a handle assembly utilizing a spring tensioner attached to a control wire, in accordance with some embodiments of the disclosure.
Figure 15:
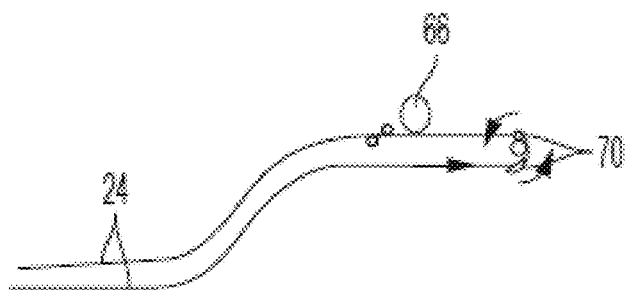
FIG. 15 illustrates a cross-sectional view of a handle assembly utilizing a pair of fixed points for securing one or more control wires to the handle assembly, in accordance with some embodiments of the disclosure.

An example embodiment of a handle assembly utilizing spring tensioner 66 attached to control wire 24 is illustrated in FIG. 14. FIG. 15 illustrates a handle assembly utilizing a pair of fixed points 70 for securing one or more control wires 24 to the handle assembly 20. FIG. 15 illustrates use of a pair of fixed points 70 for securing one or more control wires 24 to the handle assembly 20.

Methods of Manufacturing

Two embodiments are described herein for forming articulating portion 22. In one embodiment, articulating portion 22 comprises a segmented tube. The tube may be segmented, for example, by laser cutting or produced by molding the tube to a desired shape. In another embodiment, individual vertebrae 32 are connected together to form articulating portion 22. Vertebrae 32 may be connected with control wires 24 threaded therethrough. Alternatively, vertebrae 32 may snap together to create a hinge or joint effect along the neutral axis. Individual vertebrae 32 may be formed by molding or stamping.

What is claimed is:

1. A surgical instrument comprising:
   a handle assembly comprising a proximal section, an intermediate section, and a distal section, the proximal section forming a first aperture and the distal section forming a second aperture;
   a tip assembly comprising a proximal end extending through the second aperture to a distal tip comprising an articulating portion;
   one or more control wires disposed internally to the handle assembly and the tip assembly and coupled to the articulating portion;
   an articulation control extending through the first aperture, the articulation control being actuatable between a plurality of positions to deflect the articulating portion; and
   one or more guides comprising one or more posts positioned internally in the handle assembly and operable to interact with the one or more control wires during actuation of the articulation control,
   wherein a first longitudinal axis of the proximal section of the handle assembly is offset from a second longitudinal axis of the distal section of the handle assembly.

2. The surgical instrument of claim 1, further comprising a Doppler probe at the distal tip.

3. The surgical instrument of claim 2, wherein the handle assembly further comprises one or more of a spring tensioner, a fixed points system, or an idler pulley.

4. The surgical instrument of claim 1, wherein the articulating portion comprises at least one of a set of vertebrae and a segmented tube.

5. The surgical instrument of claim 4, wherein each of the set of vertebrae form at least one tapered edge and the tapered edge is cut at an angle of 20 degrees or less from a plane along a transverse axis.

6. The surgical instrument of claim 4, wherein each of the set of vertebrae form at least one tapered edge and the tapered edge forms an angled plane offset from a center of the radial axis.

7. The surgical instrument of claim 1, wherein the articulation control is a roller wheel comprising a male protrusion on one side of a rotational axis and a female recess on the opposite side.

8. The surgical instrument of claim 1, further comprising one or more of a bone grasper, soft tissue grasper/dissector, scissors, flexible forceps, or a suction/irrigation line.

9. The surgical instrument of claim 8, wherein the handle assembly further comprises a second articulation control configured to operate the bone grasper, soft tissue grasper/dissector, scissors, the flexible forceps, or the suction/irrigation line.

10. The surgical instrument of claim 1, wherein the surgical instrument is a single-use, disposable device.

11. An apparatus, comprising:
    a manipulatable elongate member, comprising
       a set of individual vertebrae connected to form a distal portion of a tube;
       a continuous tube forming a proximal portion of the tube; and
       one or more pull wires configured to interconnect the set of individual vertebrae; and
    a control handle assembly positioned at a proximal end of the manipulatable elongate member, wherein a first longitudinal axis of a proximal section of the control handle assembly is offset from a second longitudinal axis of a distal section of the control handle assembly; and
       one or more posts housed internally in the control handle assembly, the one or more posts configured to create tension on the one or more pull wires,
       wherein the manipulatable elongate member is articulatable by actuating the one or more pull wires,
       wherein the control handle assembly is configured to manipulate the one or more pull wires.

12. The apparatus of claim 11, further comprising a Doppler probe positioned at a distal tip.

13. The apparatus of claim 12, wherein the Doppler probe is an end-firing Doppler operable for detection in 360 degrees.

14. The apparatus of claim 11, further comprising at least one layer of material positioned outside the tube and forming a second tube or one or more channels positioned inside the tube.

15. The apparatus of claim 11, wherein the set of individual vertebrae are formed by at least one of hinging and molding.

16. The apparatus of claim 11, wherein a vertebra positioned at a proximal end of the set of individual vertebrae is configured with a lip for engagement with the continuous tube.

* * * * *